(12) United States Patent
Choi et al.

(10) Patent No.: US 10,945,694 B2
(45) Date of Patent: Mar. 16, 2021

(54) BREAST CANCER DIAGNOSIS DEVICE

(71) Applicants: KOREA ELECTROTECHNOLOGY RESEARCH INSTITUTE, Changwon (KR); ELECTRONICS AND TELECOMMUNICATIONS RESEARCH INSTITUTE, Daejeon (KR); THE ASAN FOUNDATION, Seoul (KR)

(72) Inventors: Young Wook Choi, Anyang (KR); Soo Yeol Lee, Daejeon (KR); Hak Hee Kim, Seoul (KR); Du Chang Heo, Seongnam (KR); Young Min Bae, Seongnam (KR); Kee Hyun Kim, Goyang (KR)

(73) Assignees: KOREA ELECTROTECHNOLOGY RESEARCH INSTITUTE, Changwon (KR); ELECTRONICS AND TELECOMMUNICATIONS RESEARCH INSTITUTE, Daejeon (KR); THE ASAN FOUNDATION, Seoul (KR)

( * ) Notice: Subject to any disclaimer, the term of this patent is extended or adjusted under 35 U.S.C. 154(b) by 419 days.

(21) Appl. No.: 15/743,212

(22) PCT Filed: Nov. 27, 2015

(86) PCT No.: PCT/KR2015/012830
§ 371 (c)(1),
(2) Date: Jan. 9, 2018

(87) PCT Pub. No.: WO2017/007086
PCT Pub. Date: Jan. 12, 2017

(65) Prior Publication Data
US 2018/0220986 A1 Aug. 9, 2018

(30) Foreign Application Priority Data

Jul. 9, 2015 (KR) .................. 10-2015-0097929

(51) Int. Cl.
*A61B 6/00* (2006.01)
*A61B 5/00* (2006.01)
(Continued)

(52) U.S. Cl.
CPC .......... *A61B 6/5247* (2013.01); *A61B 5/0035* (2013.01); *A61B 5/0073* (2013.01);
(Continued)

(58) Field of Classification Search
CPC ... A61B 5/0035; A61B 5/0073; A61B 5/0091; A61B 5/4312; A61B 5/708; A61B 6/025;
(Continued)

(56) References Cited

U.S. PATENT DOCUMENTS

2010/0030067 A1\* 2/2010 Van Beek ............ A61B 5/4381
600/425
2011/0230759 A1\* 9/2011 Muller ................... A61B 6/502
600/427
(Continued)

FOREIGN PATENT DOCUMENTS

JP 2012-505065 A 3/2012
JP 2014-533571 A 12/2014
(Continued)

OTHER PUBLICATIONS

International Search Report for PCT/KR2015/012830 filed on Nov. 27, 2015.

*Primary Examiner* — Mark D Remaly

(57) ABSTRACT

The present invention relates to a breast cancer diagnosis device. More particularly, the present invention relates to a breast cancer diagnosis device for early detection of the
(Continued)

presence or absence of breast cancer lesions inside the breast of a diagnosis subject. The breast cancer diagnosis device includes: an X-ray diagnosis unit generating an X-ray image of a diagnosis subject; an optical diagnosis unit generating an optical transmission image of the diagnosis subject; and a transfer unit which is coupled to the X-ray diagnosis unit and the optical diagnosis unit to transfer all or part of the X-ray diagnosis unit and the optical diagnosis unit, and sequentially transfer all or part of the X-ray diagnosis unit or the optical diagnosis unit toward the diagnosis subject.

16 Claims, 15 Drawing Sheets

(51) Int. Cl.
  *A61B 6/02* (2006.01)
  *A61B 6/04* (2006.01)
(52) U.S. Cl.
  CPC .......... *A61B 5/0091* (2013.01); *A61B 5/4312* (2013.01); *A61B 5/708* (2013.01); *A61B 6/025* (2013.01); *A61B 6/0414* (2013.01); *A61B 6/0435* (2013.01); *A61B 6/4208* (2013.01); *A61B 6/4417* (2013.01); *A61B 6/4452* (2013.01); *A61B 6/502* (2013.01); *A61B 6/588* (2013.01); *A61B 6/463* (2013.01); *A61B 6/466* (2013.01); *A61B 6/56* (2013.01)

(58) Field of Classification Search
  CPC ... A61B 6/0414; A61B 6/0435; A61B 6/4208; A61B 6/4417; A61B 6/4452; A61B 6/463; A61B 6/466; A61B 6/502; A61B 6/5247; A61B 6/56; A61B 6/588
  See application file for complete search history.

(56) References Cited

U.S. PATENT DOCUMENTS

| | | | | |
|---|---|---|---|---|
| 2012/0121071 | A1* | 5/2012 | Herrmann | A61B 6/56 378/194 |
| 2012/0130234 | A1* | 5/2012 | O'Connor | A61B 6/0414 600/427 |
| 2013/0083894 | A1* | 4/2013 | Niebler | A61B 6/4441 378/62 |
| 2013/0253338 | A1* | 9/2013 | Kang | A61B 5/0071 600/477 |
| 2016/0367208 | A1* | 12/2016 | Liu | A61B 6/4266 |

FOREIGN PATENT DOCUMENTS

| | | |
|---|---|---|
| KR | 10-2006-0102635 A | 9/2006 |
| KR | 10-2007-0004190 A | 1/2007 |
| KR | 10-2009-0112992 A | 10/2009 |
| KR | 10-2011-0124952 A | 11/2011 |
| WO | WO 2010/044660 A1 | 4/2010 |
| WO | WO 2013/076616 A1 | 5/2013 |

\* cited by examiner

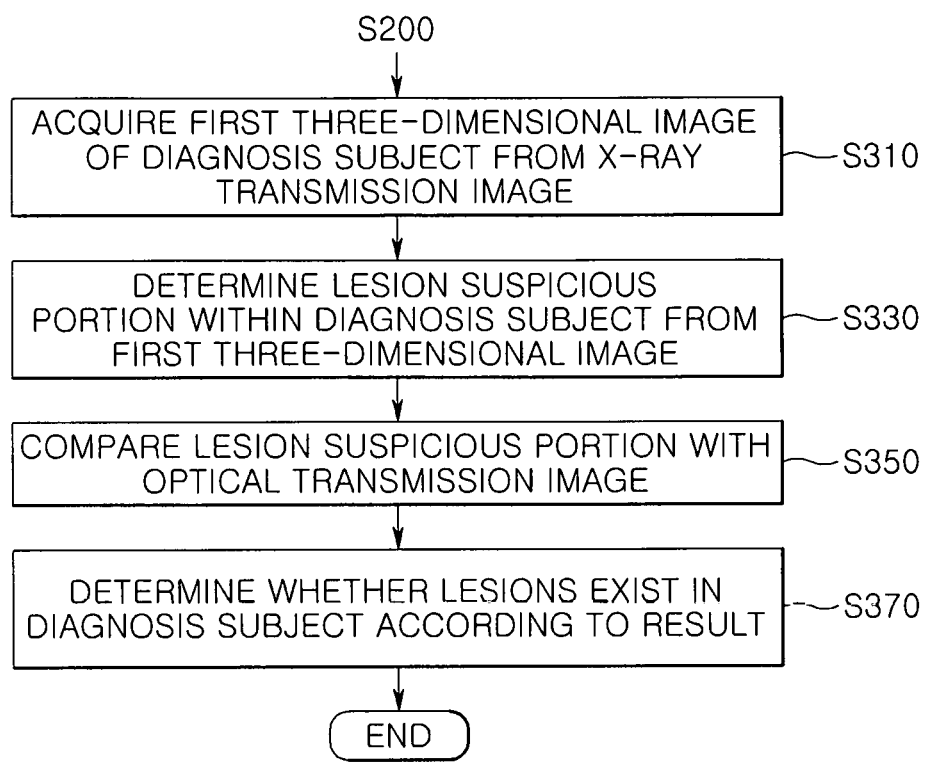

BREAST CANCER DIAGNOSIS DEVICE

CROSS REFERENCE TO RELATED APPLICATIONS PARAGRAPH

The present application is a U.S. National Stage of International Patent Application No. PCT/KR2015/012830 filed Nov. 27, 2015, which claims priority to and the benefit of Korean Patent Application No. 10-2015-0097929 filed in the Korean Intellectual Property Office on Jul. 9, 2015, the entire contents of which are incorporated herein by reference.

TECHNICAL FIELD

The present invention relates to a breast cancer diagnosis device. More particularly, the present invention relates to a breast cancer diagnosis device for early detection of the presence or absence of breast cancer lesions inside the breast of a diagnosis subject.

BACKGROUND ART

With the advent of the age of aging and the improvement of people's standard of living, there is a growing interest in early diagnosis and treatment of diseases in order to lead a healthy life, and cancer among many diseases is the number one cause of death of Korean people, and thus it is the most important factor that threatens the public health.

According to the Cancer Registration Division of the Ministry for Health, Welfare and Family Affairs, more than 130,000 new cancer patients are estimated to develop annually in Korea, and the incidence rate estimated using the number of cancer cases registered between 2003 and 2005, was 300.0 for men and 248.2 for women with respect to 100,000 people.

Also, when classified into the types of generated cancer, males have an incidence increasing in order of gastric cancer, lung cancer, liver cancer, and colon cancer, which account for 66% of all male cancer incidence, and in case of females, the incidence increases in order of breast cancer, thyroid cancer, stomach cancer, colon cancer, and lung cancer, and also, breast cancer is higher than the four major cancer incidence.

Like this, in case of females, early diagnosis and treatment of breast cancer, which has the highest incidence, is an important factor that has to be preceded for the healthy life of females.

A breast cancer diagnosis device using mammography, which is mainly used for breast cancer diagnosis in asymptomatic women, is to detect lesions inside the breast by using x-rays.

However, conventional breast cancer diagnosis devices have a problem in that detection of a breast mass, which is an important factor in the diagnosis of breast cancer, is difficult because the imaging result using the X-ray is a two-dimensional image, and thus, lesions of the interest region overlap normal tissues.

As described above, the two-dimensional image generated through the conventional breast cancer diagnosis devices has a problem in that the accuracy and the discrimination are low, and possibility of erroneous diagnosis of the breast cancer is high.

Particularly, the X-ray absorptivity of breast tissues and cancer is very difficult in distinguishing due to a small difference therebetween, and thus, the possibility of false positive or false negative is high. In reality, 30% of false positive diagnosis is present in the medical diagnosis field.

As described above, the conventional breast cancer diagnosis devices have low diagnosis accuracy, and even if there is breast cancer, in case of false negative that read normally or positively, since it overlooks the breast cancer to cause the patient to be mistaken for relieving the mistake and neglecting the breast cancer, it is a major cause of the legal problems of the medical accident while threatening the health of the patient.

Thus, it is urgently required to develop a diagnosis method of breast cancer with high accuracy so as to reduce possibility of false positive and false negative in the diagnosis of breast cancer so that unnecessary re-imaging and additional examination such as biopsy are unnecessary.

DETAILED DESCRIPTION OF THE INVENTION

Technical Problem

The present invention has been made to solve the above problems, and an object of the present invention is to provide a breast cancer diagnosis device in which an examination using a digital breast tomosynthesis (DBT) manner and an examination using a diffuse optical tomography (DOT) manner are capable of being conducted at once when a diagnosis subject (for example, a breast of the subject) is examined through the breast cancer diagnosis device to generate different three-dimensional images having high quality, thereby improving the discrimination of breast cancer lesions and significantly improving diagnosis efficiency of breast cancer.

Technical Solution

To achieve the abovementioned object, a breast cancer diagnosis device according to a preferred embodiment of the present invention includes: an X-ray diagnosis unit generating an X-ray image of a diagnosis subject; an optical diagnosis unit generating an optical transmission image of the diagnosis subject; and a transfer unit coupled to the X-ray diagnosis unit and the optical diagnosis unit to transfer all or part of the X-ray diagnosis unit and the optical diagnosis unit, and sequentially transfer all or part of the X-ray diagnosis unit or the optical diagnosis unit toward the diagnosis subject.

For example, the X-ray diagnosis unit may include: an X-ray irradiation unit generating X-rays to irradiate the X-rays onto the diagnosis subject; and an X-ray detection unit disposed to face the X-ray irradiation unit to acquire an X-ray diagnosis image of the diagnosis subject from the X-rays, which are irradiated from the X-ray irradiation unit to pass through the diagnosis subject, and the optical diagnosis unit may include: an optical irradiation unit irradiating light onto the diagnosis subject; and an optical detection unit disposed to face the optical irradiation unit to acquire an optical diagnosis image of the diagnosis subject from the light, which is irradiated from the optical irradiation unit to pass through the diagnosis subject.

Here, the transfer unit may include a horizontal transfer unit coupled to the X-ray detection unit or the optical detection unit to horizontally transfer the X-ray detection unit or the optical detection unit or the X-ray detection unit and the optical detection unit and thereby sequentially locate the X-ray detection unit and the optical detection unit in a straight line with the diagnosis subject.

The transfer unit may include a vertical transfer unit selectively coupled to one of the X-ray detection unit and the optical irradiation unit or the optical detection unit to vertically transfer one of the X-ray detection unit and the optical irradiation unit or the optical detection unit and thereby to approach the diagnosis subject.

Here, the transfer unit may be coupled to the X-ray detection unit and the optical irradiation unit or the optical detection unit, and the X-ray detection unit and the optical irradiation unit or the optical detection unit may be disposed on the same panel.

Also, the transfer unit may sequentially transfer the X-ray detection unit and the optical irradiation unit or the optical detection unit to sequentially generate the X-ray diagnosis image and the optical diagnosis image of the diagnosis subject.

Furthermore, the transfer unit may include a rotation unit allowing at least one of the X-ray diagnosis unit and the optical diagnosis unit to rotate about the diagnosis subject, and the rotation unit may include: a first rotation member disposed above the diagnosis subject to allow the X-ray irradiation unit and the optical irradiation unit or the optical detection unit to rotate about the diagnosis subject; and a second rotation member disposed below the diagnosis subject to allow the X-ray detection unit and the optical irradiation unit or the optical detection unit to rotate about the diagnosis subject.

For example, the breast cancer diagnosis device may further include compression pads pressing and fixing upper and lower portions of the diagnosis subject at a predetermined pressure so that the X-ray diagnosis unit and the optical diagnosis unit generate the X-ray image and the optical transmission image, and the compression pads may include: an upper plate disposed on the diagnosis subject to come into contact with the upper portion of the diagnosis subject; and a lower plate disposed to face the upper plate and disposed on a lower portion of the diagnosis subject to come into contact with the lower portion of the diagnosis subject.

Here, the compression pads may press the diagnosis subject that is disposed between the upper plate and the lower plate through ascending and descending of at least one of the upper plate and the lower plate.

Here, each of the compression pads may be made of a material through which wavelengths of the X-rays used for the X-ray transmission image and the light used for the optical transmission image are transmitted.

Also, one or more through-holes through which the light used for generating the optical transmission image passes may be provided in the upper plate and the lower plate constituting the compression pads, and the through-holes of the upper plate and the through-holes of the lower plate may be defined in positions corresponding to each other.

For example, the breast cancer diagnosis device may further include a mount unit disposed adjacent to the transfer unit so that one of the optical irradiation unit and the optical detection unit is disposed above the diagnosis subject.

Here, the mount unit may include: a first mount supporting the optical irradiation unit and the optical detection unit so that the optical irradiation unit and the optical detection unit are disposed in the straight line with the diagnosis subject; and a second mount supporting the optical irradiation unit and the optical detection unit so that the optical irradiation unit and the optical detection unit are disposed outside a region in which the X-ray diagnosis unit diagnoses the diagnosis subject.

A cable for supplying power and transmitting or receiving data may be provided in the optical irradiation unit or the optical detection unit, and a cable guide supporting the cable provided in the optical irradiation unit or the optical detection unit while moving the cable to prevent the cable from being bent or drooping to the bottom may be provided.

Here, the cable guide may include: a first link disposed adjacent to the transfer unit; a second link rotatably coupled to the first link; and a third link rotatably coupled to the second link and including a ring on which the cable is mounted.

The breast cancer diagnosis device may further include the lesion determination unit for fusing the optical transmission image and the X-ray transmission image, which are sequentially photographed in a state in which the diagnosis subject is constantly fixed to generate a fusion image.

Advantageous Effects

According to the present invention, the three-dimensional image of the subject, which is acquired through the digital breast tomosynthesis (DBT) manner, and the three-dimensional image of the subject, which is acquired through the diffuse optical tomography (DOT), may be complementarily utilized to confirm whether the breast cancer lesions exist, thereby improving the diagnosis efficiency of the breast cancer and reducing the unnecessary biopsy.

DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept.

FIG. 16 is a detailed flowchart illustrating operation S300 of FIG. 15.

BEST MODE

Since the present invention may have diverse modified embodiments, specific embodiments will be described in detail with reference to the accompanying drawings.

The following embodiments are provided to help comprehensive understanding of a method, an apparatus, and/or a system described in this specification. However, this is merely an example, and the present invention is not limited thereto.

In descriptions of embodiments of the present invention, detailed descriptions related to the well-known technologies will be ruled out in order not to unnecessarily obscure subject matters of the present invention. Also, terms used in the present specification are terms defined in consideration of functions according to embodiments, and thus the terms may be changed according to the intension or usage of a user or operator. Therefore, the terms should be defined on the basis of the overall contents of this specification. The tams used in the present specification are merely used to describe particular embodiments, and are not intended to limit the present invention. An expression used in the singular encompasses the expression in the plural, unless it has a clearly different meaning in the context. In the present specification, it is to be understood that terms such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Also, it will be understood that although the terms of first and second are used herein to describe various elements, these elements should not be limited by these terms. The terms are used only for the purpose of distinguishing one component from another.

Hereinafter, preferred embodiments of the present invention will be described in detail with reference to the accompanying drawings.

Figure 1:
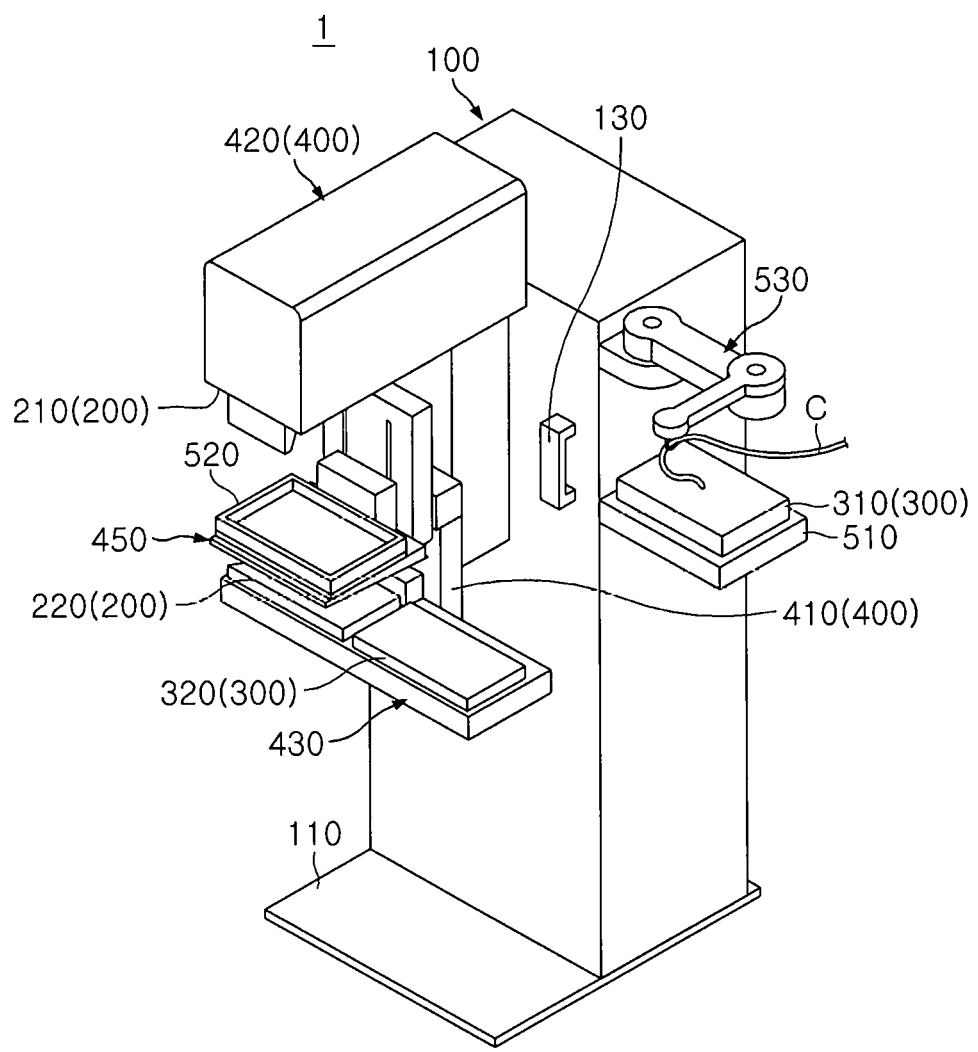
FIG. 1 is a perspective view of a breast cancer diagnosis device according to an embodiment of the present invention.
Figure 2:
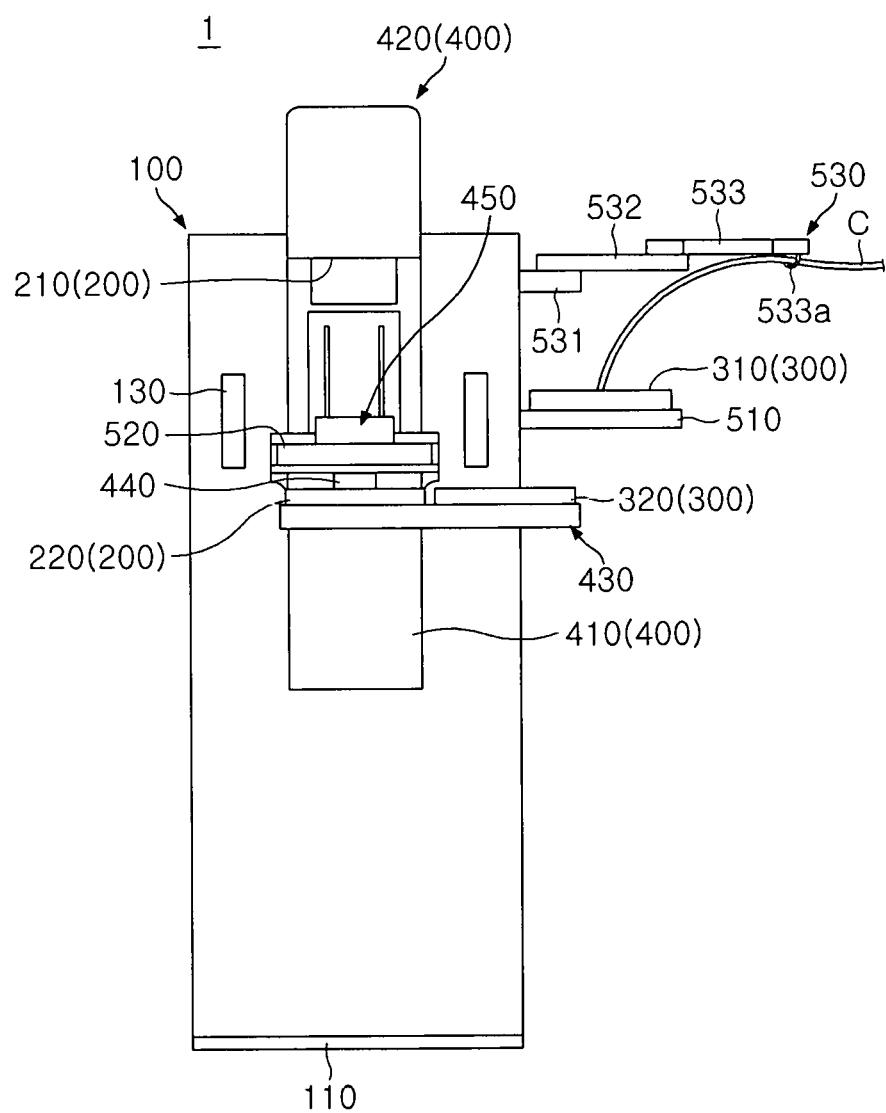
FIG. 2 is a front view of the breast cancer diagnosis device according to an embodiment of the present invention.
Figure 3:
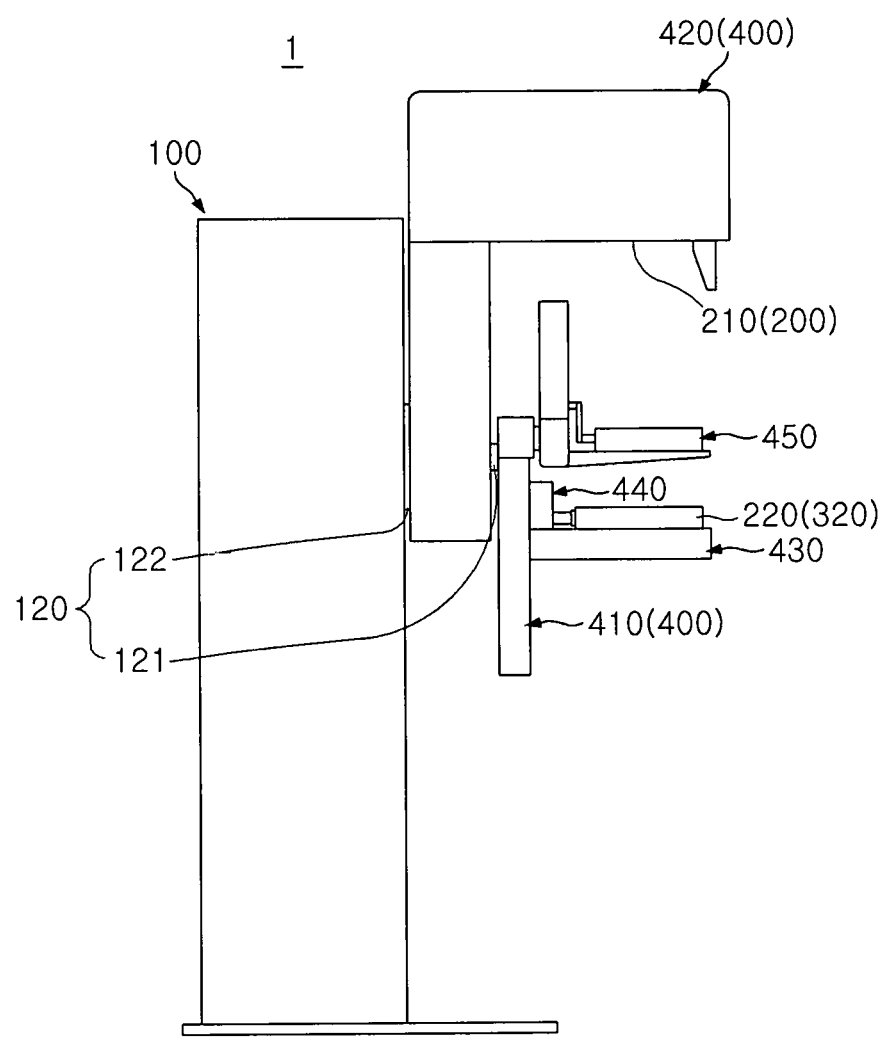
FIG. 3 is a side view of the breast cancer diagnosis device according to an embodiment of the present invention.
Figure 4:
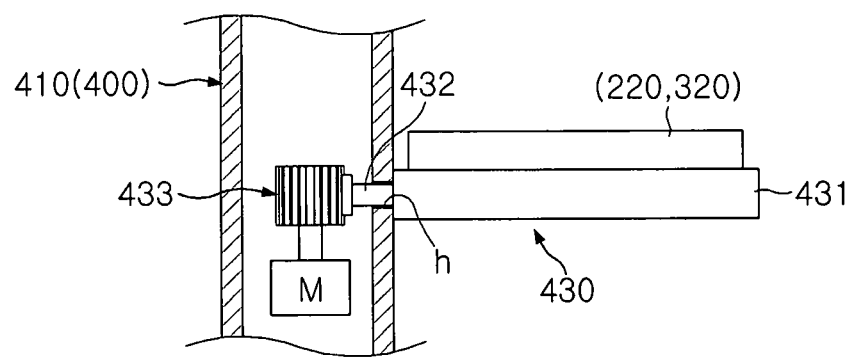
FIG. 4 is a conceptual view illustrating a horizontal transfer unit of the breast cancer diagnosis device according to an embodiment of the present invention.
Figure 5:
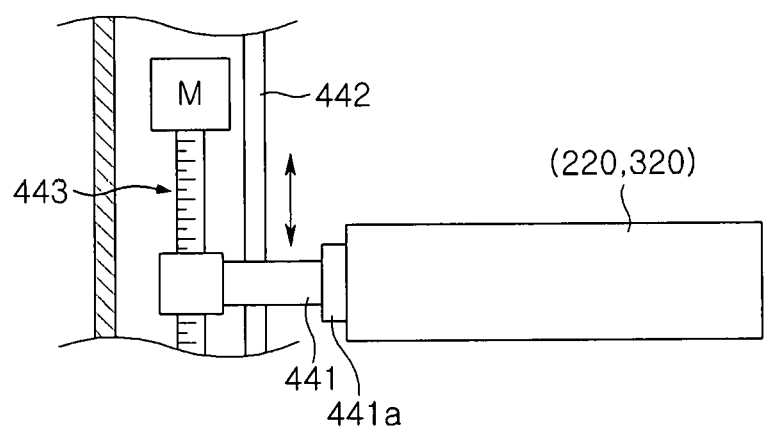
FIG. 5 is a conceptual view illustrating a vertical transfer unit of the breast cancer diagnosis device according to an embodiment of the present invention.
Figure 6:
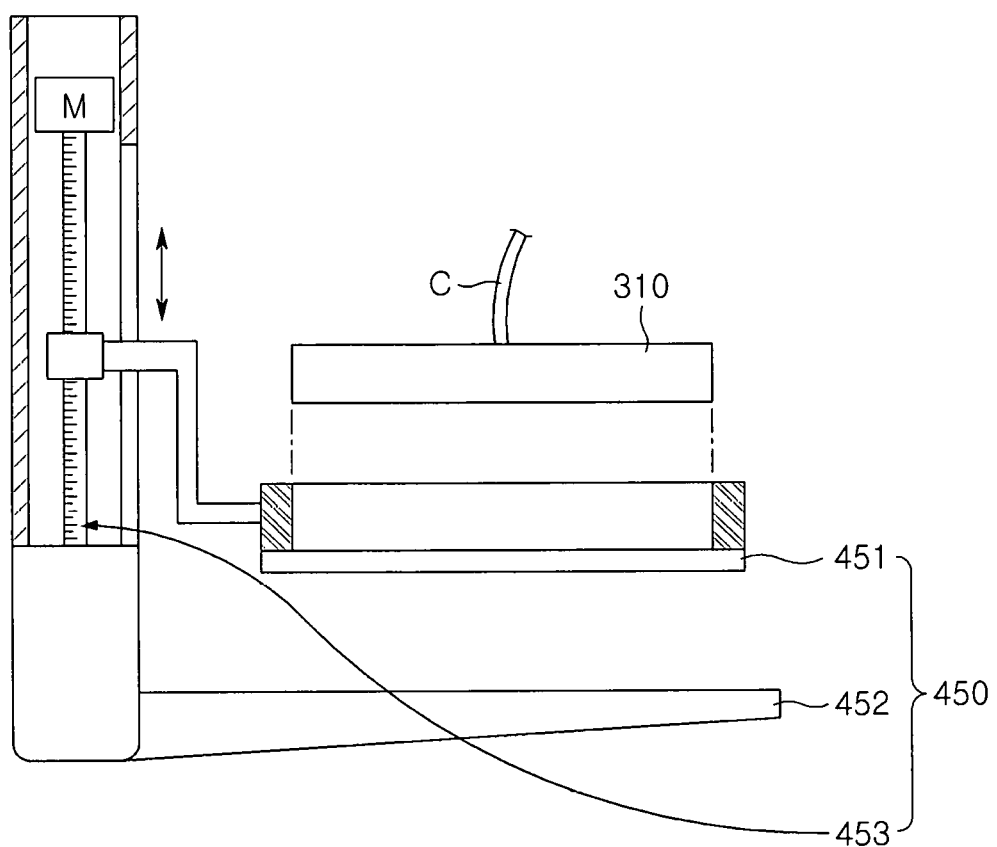
FIG. 6 is a conceptual view illustrating compression pads of the breast cancer diagnosis device according to an embodiment of the present invention.
Figure 7:
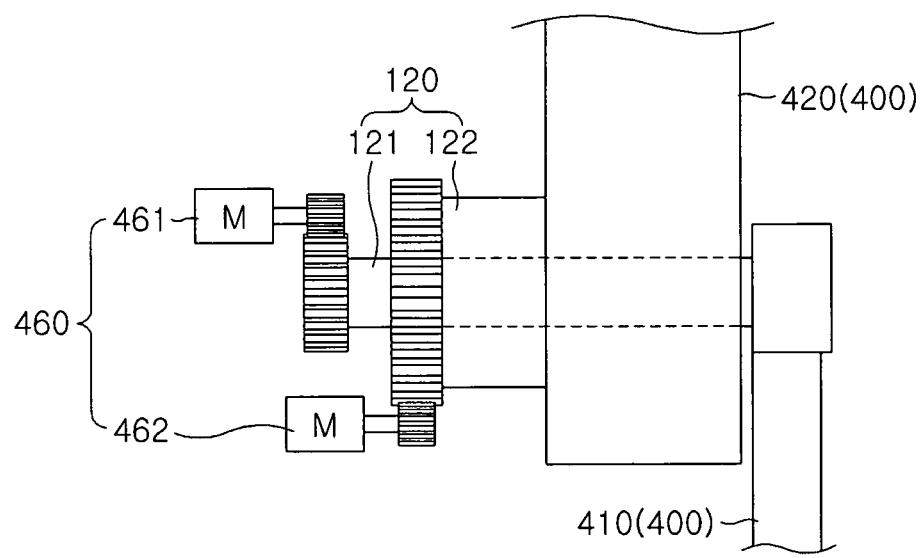
FIG. 7 is a conceptual view illustrating a rotation unit of the breast cancer diagnosis device according to an embodiment of the present invention.
Figure 8:
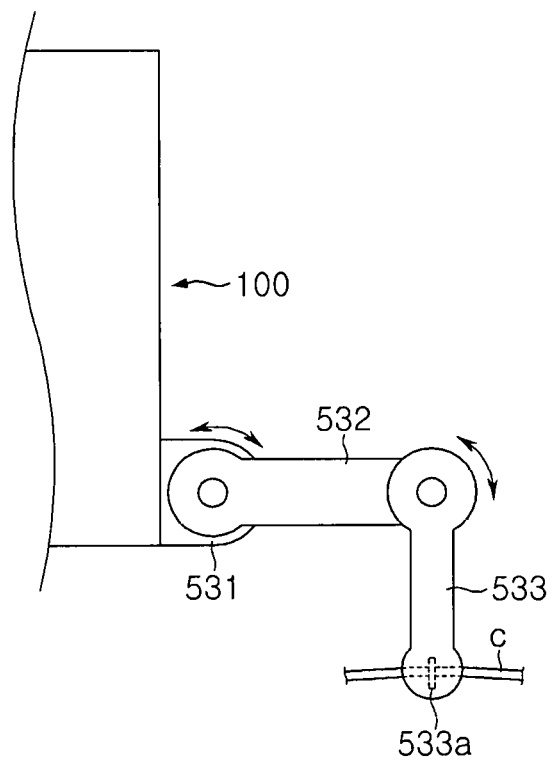
FIG. 8 is a conceptual view illustrating a cable guide of the breast cancer diagnosis device according to an embodiment of the present invention.
Figure 9A:
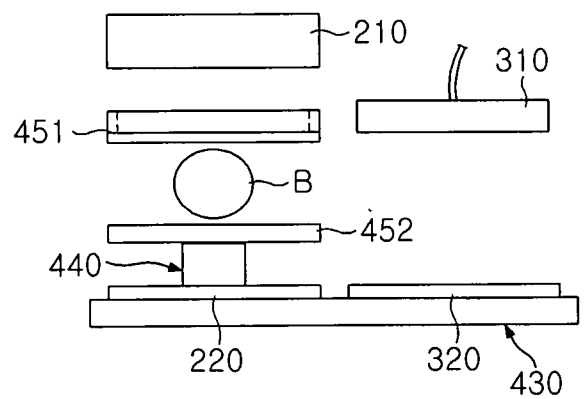
FIGS. 9A to 9F are conceptual views illustrating an operation process of the breast cancer diagnosis device according to an embodiment of the present invention.
Figure 9B:
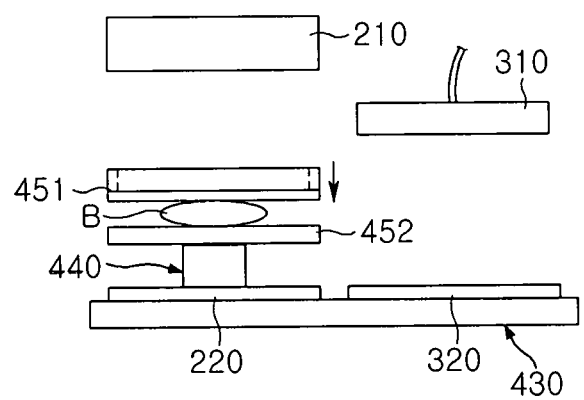
Figure 9C:
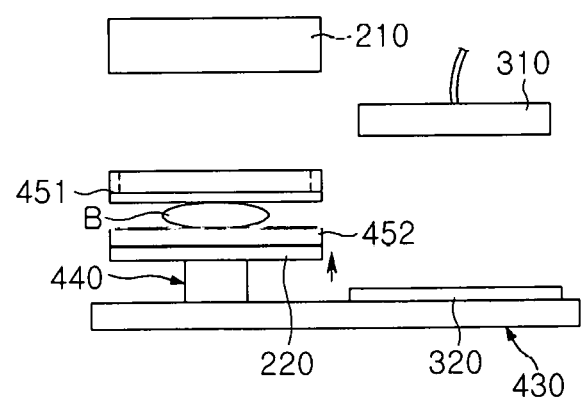
Figure 9D:
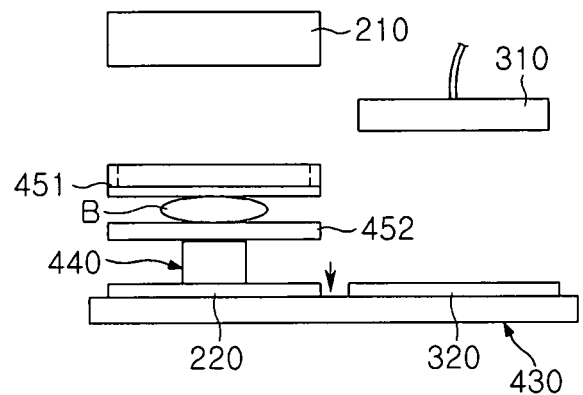
Figure 9E:
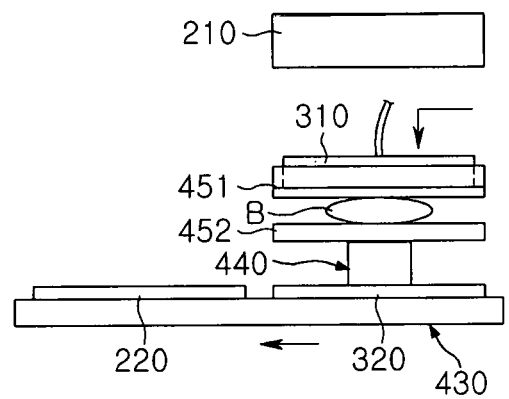
Figure 9F:
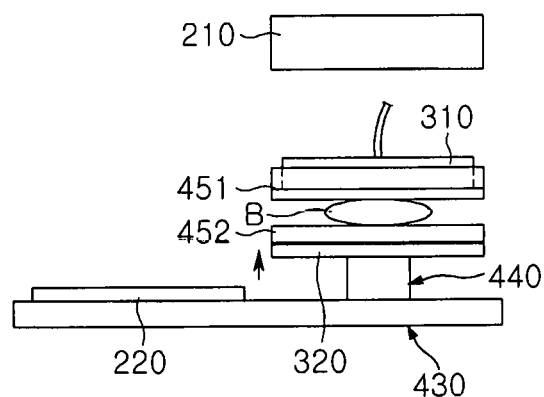

FIG. 1 is a perspective view of a breast cancer diagnosis device according to an embodiment of the present invention, FIG. 2 is a front view of the breast cancer diagnosis device according to an embodiment of the present invention, FIG. 3 is a side view of the breast cancer diagnosis device according to an embodiment of the present invention, FIG. 4 is a conceptual view illustrating a horizontal transfer unit of the breast cancer diagnosis device according to an embodiment of the present invention, FIG. 5 is a conceptual view illustrating a vertical transfer unit of the breast cancer diagnosis device according to an embodiment of the present invention, FIG. 6 is a conceptual view illustrating compression pads of the breast cancer diagnosis device according to an embodiment of the present invention, FIG. 7 is a conceptual view illustrating a rotation unit of the breast cancer diagnosis device according to an embodiment of the present invention, and FIG. 8 is a conceptual view illustrating a cable guide of the breast cancer diagnosis device according to an embodiment of the present invention.

Referring to FIGS. 1 to 3, a breast cancer diagnosis device according to an embodiment of the present invention includes a main body 100, an X-ray diagnosis unit 200, an optical diagnosis unit 300, and a transfer unit 400.

The main body 100 may include a bottom part 110 having one side coupled to the transfer unit 400 and supporting the ground so that the main body 100 stably stands up. The transfer unit 400 may be rotatably coupled to the main body 100. Particularly, the main body 100 may be provided with a rotation shaft 120 that is coupled to the transfer unit 400 to rotate.

The main body 100 may include a handle 130. The handle 130 may be disposed on each of both sides of a front surface of the main body 100. For example, in a state in which a target B to be diagnosed (hereinafter, referred to as a diagnosis subject) of a person to be diagnosed is disposed adjacent to the X-ray diagnosis unit 200 or the optical diagnosis unit 300, the person may grasp the handle 130 to maintain the position of the diagnosis subject B by using the handle 130.

The X-ray diagnosis unit 200 may generate an X-ray image of the diagnosis subject B. The X-ray diagnosis unit 200 may be installed on the transfer unit 400. The X-ray diagnosis unit 200 may include an X-ray irradiation unit 210 and an X-ray detection unit 220.

The X-ray irradiation unit 210 may generate X-rays to irradiate the X-rays onto the diagnosis subject B. Here, the X-ray irradiation unit 210 may be an X-ray tube. The X-ray irradiation unit 210 may be installed in an upper portion of the transfer unit 400. In other words, the X-ray irradiation unit 210 may be installed on the transfer unit 400 above the diagnosis subject B. The X-ray irradiation unit 210 may intermittently or continuously rotate to irradiate the X-rays onto the diagnosis subject B according to an angle range (for example, −21 degrees to 21 degrees) that is previously set by the transfer unit 400. For example, the X-ray irradiation unit 210 may intermittently rotates about the diagnosis subject B. Particularly, the X-ray irradiation unit 210 may repeatedly perform stop and rotation with respect to a predetermined angle to rotate. Here, when the X-ray irradiation unit 210 stops after rotating to a predetermined angle, the X-ray irradiation unit 210 may irradiate the X-rays toward the diagnosis subject B. Alternatively, when the X-ray irradiation unit 210 rotates to a preset range to reach a predetermined angle, the X-ray irradiation unit 210 may irradiate the X-rays toward the diagnosis subject B.

The X-ray detection unit 220 may be disposed to face the X-ray irradiation unit 210. For example, the X-ray detection unit 220 may be installed on the transfer unit 400 below the diagnosis subject B. The X-ray detection unit 220 may acquire an X-ray diagnosis image of the diagnosis subject B from the X-rays passing through the diagnosis subject B after being irradiated from the X-ray irradiation unit 210. The X-ray detection unit 220 may datafy the X-ray transmission images of the diagnosis subject B on the basis of the X-rays irradiated from the X-ray irradiation unit 210 onto the diagnosis subject B at various angles.

The X-ray detection unit 220 may be a digital-type semiconductor flat panel detector. The semiconductor flat panel detector may include a plurality of sensors, which are disposed in the form of a matrix. As described above, the semiconductor flat panel detector may have advantages such as a high resolution, a wide dynamic range, high electrical signal generation, and easy data processing when compared to the conventional films.

Thus, real-time processing and playback of the X-ray diagnosis images may be enabled, and also, high-resolution X-ray diagnosis image may be acquired by using a relatively small amount of X-rays.

The X-ray irradiation unit 210, the X-ray detection unit 220, and the diagnosis subject B may be disposed in a straight line. Thus, a focus of the X-rays irradiated from the X-ray irradiation unit 210 may be coincident with the diagnosis subject B to acquire a high-quality X-ray diagnosis image without error with respect to the diagnosis subject B. Here, the diagnosis subject B may be preferably disposed between the X-ray irradiation unit 210 and the X-ray detection unit 220.

The optical diagnosis unit 300 may generate an optical transmission image of the diagnosis subject B. The optical diagnosis unit 300 may include an optical irradiation unit 310 and an optical detection unit 320.

The optical irradiation unit 310 may irradiate light onto the diagnosis subject B. For example, the optical irradiation unit 310 may irradiate infrared light onto the diagnosis subject B. Particularly, the optical irradiation unit 310 may irradiate infrared light having a wavelength of 785 nm, 800 nm, or 850 nm onto the diagnosis subject B. The optical irradiation unit 310 may be constituted by a plurality of light sources 311 to have a predetermined pattern. The optical irradiation unit 310 may be installed in an upper portion of the transfer unit 400. In other words, the optical irradiation unit 310 may be installed on the transfer unit 400 above the diagnosis subject B. Alternatively, the optical irradiation unit 310 may be installed in a lower portion of the transfer unit 400 below the diagnosis subject B.

The optical detection unit 320 may be disposed to face the optical irradiation unit 310. For example, the optical detection unit 320 may be installed on the transfer unit 400 so that the optical detection unit 320 is disposed on an opposite side of the optical irradiation unit 310 with respect to the diagnosis subject B. The optical detection unit 320 may acquire an optical transmission image of the diagnosis subject B from the light passing through the diagnosis subject B after being irradiated from the optical irradiation unit 310. For example, the optical detection unit 320 may be constituted by a plurality of photodiodes 321 to have a predetermined pattern. Preferably, the plurality of photodiodes 321 provided in the optical detection unit 320 may be disposed to correspond to the plurality of light sources 311 provided in the optical irradiation unit 310. Here, each of the photodiodes 321 may be an avalanche photo diode (APD).

The transfer unit 400 may be coupled to the main body 100. The transfer unit 400 may be coupled to the X-ray diagnosis unit 200 and the optical diagnosis unit 300 to transfer the X-ray diagnosis unit 200 and the optical diagnosis unit 300. Here, the transfer unit 400 may sequentially transfer the X-ray diagnosis unit 200 and the optical diagnosis unit 300 toward the diagnosis subject B.

Also, the transfer unit 400 may be configured so that the whole or a portion of the X-ray diagnosis unit 200 and the optical diagnosis unit 300 are disposed on the same panel. In detail, as illustrated in FIG. 1, the optical irradiation unit 310 or the optical detection unit 320 together with the X-ray detection unit 200 may be disposed on one panel.

Thus, the transfer unit 400 may transfer the X-ray detection unit 200 to approach the diagnosis subject in a state in which the diagnosis subject is constantly fixed so that the X-ray diagnosis image is generated and then transfer the optical irradiation unit 310 or the optical detection unit 320 to approach the diagnosis subject so that the optical diagnosis image is sequentially generated. Thus, the X-ray diagnosis image and the optical diagnosis image may be effectively generated in the state in which the diagnosis subject is fixed.

The transfer unit 400 may include a first driving base 410, a second driving base 420, a horizontal transfer unit 430, a vertical transfer unit 440, compression pads 450, and a rotation unit 460.

The first driving base 410 is rotatably coupled to the main body 100. For example, the first driving base 410 may be coupled to the rotation shaft 120 of the main body 100 to rotate about the rotation shaft 120. Particularly, the first driving base 410 may rotate through power provided from the rotation unit 460. Although described below, the first driving base 410 may provide a path along which the vertical transfer unit 440 ascends or descends.

The second driving base 420 is coupled to the main body 100 above the first driving base 410. For example, the second driving base 420 may be rotatably coupled to the main body 100 and have a "⌐" shape. Particularly, the second driving base 420 may be coupled to the rotation shaft 120 of the main body 100 to rotate about the rotation shaft 120. The first driving base 410 may rotate through power provided from the rotation unit 460. The X-ray irradiation unit 210 may be disposed on the second driving base 420. For example, the X-ray irradiation unit 210 may be coupled to an upper portion of the second driving base 420 to irradiate the X-rays onto the diagnosis subject B.

The horizontal transfer unit 430 may be coupled to the first driving base 410 so that the horizontal transfer unit 430 is disposed below the diagnosis subject B. The horizontal transfer unit 430 is coupled to the X-ray irradiation unit 230 and the optical irradiation unit 310 or the optical detection unit 320. For example, the X-ray detection unit 220 and the optical irradiation unit 310 or the X-ray detection unit 220 and the optical detection unit 320 are selectively disposed on the horizontal transfer unit 430. For convenience of description, it is assumed that the X-ray detection unit 220 and the optical detection unit 320 are coupled to the horizontal transfer unit 430.

The horizontal transfer unit 430 may horizontally transfer the X-ray detection unit 220 and the optical detection unit 320. Thus, the horizontal transfer unit 430 may gradually approach the diagnosis subject B. Particularly, the horizontal transfer unit 430 may horizontally transfer the X-ray detection unit 220 and the optical detection unit 320 so that one of the X-ray detection unit 220 and the optical detection unit 320 is disposed in a straight line with the diagnosis subject B.

For this, the horizontal transfer unit 430 may include a horizontal transfer member 431 that allows the X-ray detection unit 220 and the optical detection unit 320 to be disposed in the straight line, a first rail 432 that provides a moving path to the horizontal transfer member 431, and a first driving member 433 coupled to the first rail 432 to provide power so that the horizontal transfer member 431 moves along the first rail 432.

The horizontal transfer member 431 may have a plate shape having a predetermined area. For example, the horizontal transfer member 431 may have an area so that the X-ray detection unit 220 and the optical detection unit 320 are disposed on a top surface thereof. The horizontal transfer member 431 may be coupled to the first driving base 410. Particularly, the horizontal transfer member 431 may be disposed on one surface of the first driving base 410 and be coupled to straightly move along a longitudinal direction of the horizontal transfer member 431.

The first rail 432 may be disposed at a position that comes into contact with the horizontal transfer member 431 and the first driving base 410. For example, the first rail 432 may be disposed on a side surface of the horizontal transfer member 431 in the longitudinal direction and may have a length that is enough so that centers of the X-ray detection unit 220 and the optical detection unit 320 are disposed in a straight line with a center of the diagnosis subject B.

For example, the first rail 432 may protrude from the side surface of the horizontal transfer member 431. Also, the first driving base 410 may have a hole h in which the first rail 432 is seated.

The first driving member 433 may be installed on the horizontal transfer member 431 or the first driving base 410. The first driving member 433 may be coupled to the first rail 432. The first driving member 433 provides power so that the horizontal transfer member 431 linearly reciprocates in a horizontal direction along the first rail 432.

For example, a rack gear may be disposed on one surface of the first rail 432, and a pinion gear may be disposed on the first driving member 433 to correspond to the rack gear. In a state in which the rack gear and the pinion gear are engaged with each other, the driving member 433 may provide rotation force to transfer the horizontal transfer member 431 along the first rail 432.

On the other hand, the horizontal transfer unit 430 may transfer the horizontal transfer member 431 in the horizontal direction along the first rail 432 by using a bolt, a ball screw, an LM guide, and the like. That is, the first driving member 433 may convert a rotation motion into a linear motion to transfer the horizontal transfer member 431 in the horizontal direction. For this, a motor may be provided in the first driving member 433.

The vertical transfer unit 440 may be coupled to the first driving base 410 to allow one of the X-ray detection unit 220, the optical irradiation unit 310, and the optical detection unit 320, which are disposed on the horizontal transfer unit, to ascend or descend along the movement of the horizontal transfer unit 430.

For example, the vertical transfer unit 440 may allow one of the X-ray detection unit 220, the optical irradiation unit 310, and the optical detection unit 320, which are disposed in the straight line with the diagnosis subject B by the horizontal transfer unit 430, to ascend and approach the diagnosis subject B.

For this, the vertical transfer unit 440 may be coupled to the first driving base 410 and may include a vertical transfer member 441 selectively coupled to one of the X-ray detection unit 220, the optical irradiation unit 310, and the optical detection unit 320, a second rail 442 providing a vertical movement path to the vertical transfer member 441, and a second driving member 443 coupled to the second rail 442 to allow the vertical transfer member 441 to ascend or descend along the second rail 442.

One side of the vertical transfer member 441 is coupled to ascend or descend along the first driving base 410. The vertical transfer member 441 is coupled to one of the X-ray detection unit 220, the optical irradiation unit 310, and the optical detection unit 320, which are transferred through the horizontal transfer unit 430. For example, the vertical transfer member 441 is coupled to one of the X-ray detection unit 220, the optical irradiation unit 310, and the optical detection unit 320, which are transferred to a lower side of the diagnosis subject B through the horizontal transfer unit 430. For this, the vertical transfer member 441 may further include a coupling member 441a coupled to one of the X-ray detection unit 220, the optical irradiation unit 310, and the optical detection unit 320. Alternatively, each of the X-ray detection unit 220, the optical irradiation unit 310, and the optical detection unit 320 may include a constituent coupled to the vertical transfer member 441.

The second rail 442 is disposed in a direction perpendicular to the first driving base 410. The second rail 442 may be a groove defined in the first driving base 410. A protrusion into which the second rail 442 is inserted may be disposed on the vertical transfer member 441.

The second driving member 443 may be installed on the first driving base 410. The second driving member 443 provides power so that the vertical transfer member 441 linearly reciprocates in a vertical direction along the second rail 442.

For example, the second driving member 443 may be constituted by a spiral shaft penetrated and screw-coupled to the vertical transfer member 441 inserted into the second rail 442 and a motor through which the spiral shaft rotates. Alternatively, the second driving member 443 may elevate the vertical transfer member 441 through the LM guide.

The compression pads 450 may be coupled to the first driving base 410 so that the compression pads 450 are disposed above the horizontal transfer unit 430. A predetermined pressure may be applied to upper and lower portions of the diagnosis subject B to fix the diagnosis subject B so that the X-ray diagnosis unit 200 and the optical diagnosis unit 300 generate the X-ray image and the optical transmission image of the diagnosis subject B.

The compression pads 450 may include an upper plate 451 disposed on the diagnosis subject B to come into contact with the upper portion of the diagnosis subject B, a lower plate 452 disposed to face the upper plate 451 and disposed on a lower portion of the diagnosis subject B to come into contact with the lower portion of the diagnosis subject B, and a third driving member 453 that allows the upper plate 451 and the lower plate 452 to vary in height to press the diagnosis subject B disposed between the upper plate 451 and the lower plate 452. Here, the third driving member 453 has the same mechanism as the above-described second driving member 443, and thus, its detailed description will be omitted.

A plurality of first through-holes 451a defined to correspond to the plurality of light sources 311 having the predetermined pattern may be defined in the upper plate 451, and a plurality of second through-holes 452a defined to correspond to the first through-holes 451a may be defined in the lower plate 452. Since the plurality of light sources 311 are disposed to correspond to the photodiodes 321, it is obvious that the second through-holes 452a and the photodiodes 321 correspond to each other. As described above, in the light source 311, first and second through-holes 413a1 and 13b1, and the photodiodes 321, which are disposed to correspond to each other, when the light source 311 irradiates light, the light may be provided to the photodiodes 321 by passing through the first and second through holes 413a1 and 13b1 to acquire an optical transmission image.

If the first through-hole 451a and the second through-hole 452a are not provided in the upper plate 451 and the lower plate 452, an anti reflection coating layer for preventing the light (infrared light) irradiated from the light source 311 from being reflected may be disposed on surfaces of the upper plate 451 and the lower plate 452.

The rotation shaft 120 coupled to the main body 100 may include a first rotation shaft 121 and a second rotation shaft 122. The first rotation shaft 121 may be coupled to the first driving base 410, and the second rotation shaft 122 is coupled to the second driving base 420. The first rotation shaft 121 and the second rotation shaft 122 are concentrically disposed. For example, the second rotation shaft 122 may be disposed to be inserted into the first rotation shaft 121. On the other hand, the first rotation shaft 121 may be disposed to be inserted into the second rotation shaft 122.

The rotation unit 460 may allow at least one of the first driving base 410 and the second driving base 420 to rotate about the diagnosis subject B. For example, the rotation unit 460 may include a first rotation member 461 and a second rotation member 462 in the main body 100 to allow each of the first driving base 410 and the second driving base 420 to rotate.

The first rotation member 461 may allow the first driving base 410 to rotate about the diagnosis subject B. For example, the first rotation member 461 may be disposed in the main body 100 to provide power to the first driving base 410. Particularly, the first rotation member 461 may be installed in the main body 100 to provide power to the first rotation shaft 121 coupled to the first driving base 410.

The second rotation member 462 may allow the second driving base 420 to rotate about the diagnosis subject B. For example, the second rotation member 462 may be disposed in the main body 100 to provide power to the second driving base 420. Particularly, the second rotation member 462 may be installed in the main body 100 to provide power to the second rotation shaft 122 coupled to the second driving base 420.

The first rotation member 461 and the second rotation member 462 may allow the first driving base 410 and the second driving base 420 to rotate around the diagnosis subject B in a state in which the first driving base 410 and the second driving base 420 are disposed in the straight line with the diagnosis subject B. For example, when the first driving base 410 rotates to a right side by the first rotation member 461, the second driving base 420 may rotate to a left side by the second rotation member 462, and the first driving base 410 and the second driving base 420 may be maintained in the straight line. That is to say, when one of the first rotation member 461 and the second rotation member 462 rotates at a predetermined angle, the rest may rotate at an angle corresponding to the predetermined angle in an opposite direction.

Alternatively, only one of the first rotation member 461 and the second rotation member 462 may rotate about the diagnosis subject B. For example, the first rotation member 461 may continuously or intermittently rotate at a predetermined angle about the diagnosis subject B. Here, the second rotation member 462 does not rotate.

That is, when the first and second rotation shafts 121 and 122 rotate by the first and second rotation members 461 and 462, the first and second driving bases 410 and 420 rotate along the first and second rotation shafts 121 and 122. As the first and second driving bases 410 and 420 rotate, the X-ray diagnosis unit 200 and the optical diagnosis unit 300 rotate about the diagnosis subject B. Particularly, as the first and second driving bases 410 and 420 rotate, since at least two of the X-ray irradiation unit 210, the X-ray detection unit 220, the optical irradiation unit 310, and the optical detection unit 320 rotate about the diagnosis subject B, the diagnosis subject B may be measured for various angles and positions.

The mount unit 500 may be disposed adjacent to the transfer unit 400 so that one of the optical irradiation unit 310 or the optical detection unit 320 is disposed above the diagnosis subject B. For example, the mount unit 500 may be disposed on the main body 100.

The mount unit 500 may include a first mount 510 and a second mount 520.

The first mount 510 may support the optical irradiation unit 310 or the optical detection unit 320 in the straight line with the diagnosis subject B. For example, the first mount 510 may be disposed on the upper plate 451 of each of the compression pads 450. Particularly, the first mount 510 may be a frame protruding along an edge of the upper plate 451. For example, the optical irradiation unit 310 or the optical detection unit 320 may be inserted into, coupled to, or mounted on the first mount 510.

The optical irradiation unit 310 or the optical detection unit 320 may be disposed on the second mount 520 outside a region in which the X-ray diagnosis unit 300 diagnoses the diagnosis subject B. For example, the second mount 520 may be coupled to the side surface of the main body 100 to support the optical irradiation unit 310 or the optical detection unit 320. The second mount 520 may preferably have a predetermined area for supporting the optical irradiation unit 310 or the optical detection unit 320.

A cable C for transmitting or receiving data and providing power may be provided in the optical irradiation unit 310 or the optical detection unit 320.

The mount unit 500 may include a cable guide 530 that supports the cable C while moving to prevent the cable C provided in the optical irradiation unit 310 or the optical detection unit 320 from being bent or drooping to the bottom.

The cable guide 530 may include a first link 531, a second link 532, and a third link 533.

The first link 531 may be disposed adjacent to the transfer unit 400. For example, the first link 531 may have one side that is installed on the side surface of the main body 100. The second link 532 may be rotatably coupled to the first link 531. For example, the first link 531 and the second link 532 may be hinge-coupled to each other. The third link 533 may be rotatably coupled to the second link 532.

The third link 533 may include a ring 533a holding the cable C. The ring 533a may be partially cut to be opened to hold the cable C. Alternatively, the ring 533a may have a structure, in which a portion of the ring 533a rotates about an axis and opened, such as a karabiner.

Mode of the Invention

The third link 533 may include a ring 533a holding the cable C. The ring 533a may be partially cut to be opened to hold the cable C. Alternatively, the ring 533a may have a structure, in which a portion of the ring 533a rotates about an axis and opened, such as a karabiner.

Figure 10:
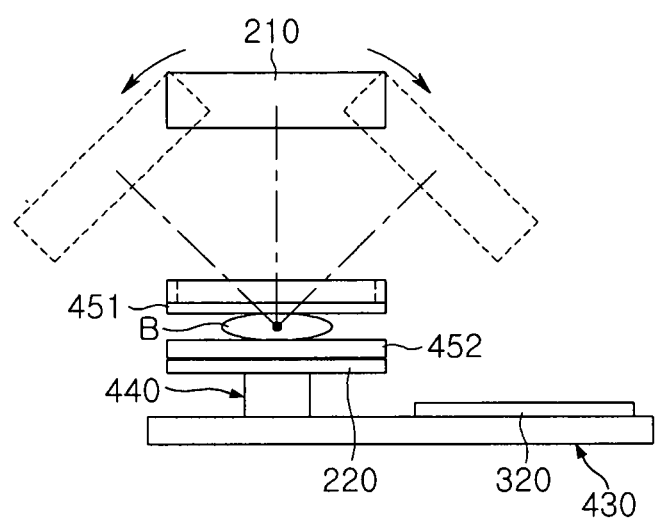
FIG. 10 is a conceptual view illustrating an operation process of an X-ray irradiation unit of the breast cancer diagnosis device according to an embodiment of the present invention.
Figure 11A:
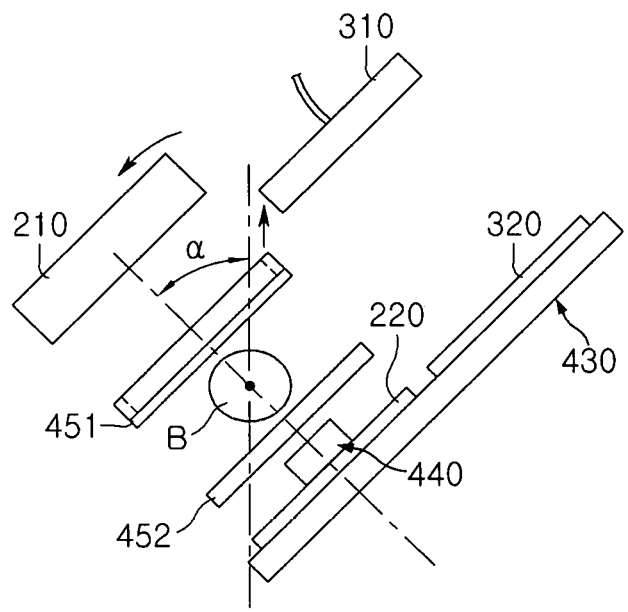
FIGS. 11A and 11B are conceptual views illustrating an operation process of the breast cancer diagnosis device according to an embodiment of the present invention.
Figure 11B:
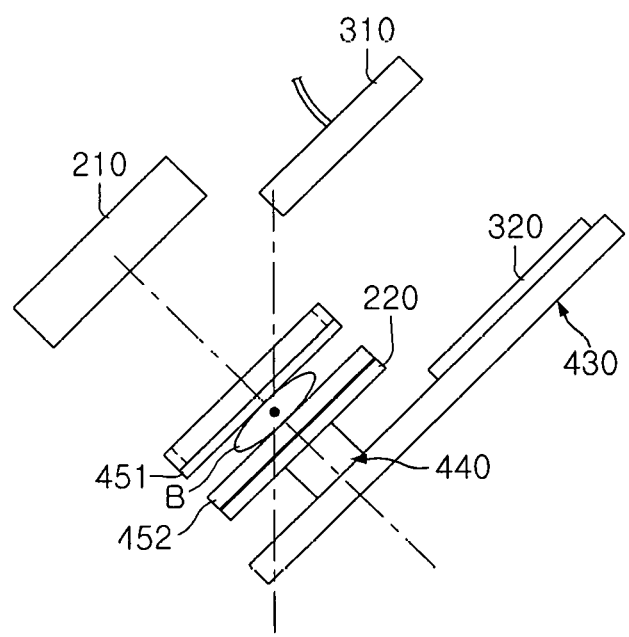

FIGS. 9A to 9F are conceptual views illustrating an operation process of the breast cancer diagnosis device according to an embodiment of the present invention, FIG. 10 is a conceptual view illustrating an operation process of the X-ray irradiation unit of the breast cancer diagnosis device according to an embodiment of the present invention, and FIGS. 11A and 11B are conceptual views illustrating an operation process of the breast cancer diagnosis device according to an embodiment of the present invention.

Referring to FIGS. 9A to 9F, 10, 11A and 11B, an operation effect of a breast cancer diagnosis device 1 according to an embodiment of the present invention will be described.

First, to examine the diagnosis subject B by using the breast cancer diagnosis device 1, the diagnosis subject B is disposed between the compression pads 450. Here, the diagnosis subject B may be breast.

When the diagnosis subject B is disposed between the upper plate 451 and the lower plate 452 of the compression pads 450, the third driving member 453 operates to allow one of the upper plate 451 or the lower plate 452 to ascend or descend toward the diagnosis subject B. For convenience of description, it is assumed that the upper plate 451 ascends or descends by the third driving member 453.

The upper plate 451 descends by the third driving member 453 to come into contact with an upper portion of the diagnosis subject B and thereby to press the upper portion of the diagnosis subject B at a predetermined pressure. Here, the pressure applied to the diagnosis subject B by the upper plate 451 may be adjusted according to a size or state of the diagnosis subject B.

When the diagnosis subject B is fixed in the pressed state through the compression pads 450, the X-ray diagnosis unit 200 examines the diagnosis subject B. Particularly, the X-ray irradiation unit 210 irradiates the X-rays to the diagnosis subject B, and the X-ray detection unit 220 generates an X-ray transmission image through the X-rays provided by passing through the diagnosis subject B.

Here, the X-ray irradiation unit 210 and the X-ray detection unit 220 may be disposed in the straight line with the diagnosis subject B, and the X-ray detection unit 220 is in a state of approaching the lower portion of the diagnosis subject B by the vertical transfer unit 440. Also, the optical irradiation unit 310 is in a state of being mounted on the second mount 520.

Then, the X-ray irradiation unit 210 may rotate at a predetermined angle about the diagnosis subject B to irradiate the X-rays onto the diagnosis subject B. Particularly, to allow the X-ray irradiation unit 210 to rotate about the diagnosis subject B, the first rotation member 461 provides power to the first rotation shaft 121. Thus, the first rotation shaft 121 rotates to allow the first driving base 410 to rotate and also to allow the X-ray irradiation unit 210 coupled to the first driving base 410 to rotate. Here, the first rotation member 461 may control the power provided to the first rotation shaft 121 so as to allow the X-ray irradiation unit 210 to continuously or intermittently rotate at a predetermined angle.

The X-ray diagnosis unit 200 may examine the diagnosis subject B in the state in which the X-ray diagnosis unit 200 rotates at the predetermined angle according to situations.

In detail, each of the X-ray irradiation unit 210 and the X-ray detection unit 220 rotates at a predetermined angle while maintaining the state in which the X-ray irradiation unit 210 and the X-ray detection unit 220 are disposed in the straight line with the diagnosis subject B. Here, since the compression pads 450 are in the state of being disposed on the transfer unit 400, the X-ray irradiation unit 210 and the X-ray detection unit 220 rotate together.

In this state, the diagnosis subject B may be disposed to be pressed and fixed between the compression pads 450, and the X-ray irradiation unit 210 and the X-ray detection unit 220 may irradiate the X-rays to the diagnosis subject B to obtain the X-ray transmission image. Also, in this state, the X-ray irradiation unit 210 may continuously or intermittently rotate about the diagnosis subject B by the first rotation member 461 to examine the diagnosis subject B.

When the examination of the diagnosis subject B is completed by the X-ray diagnosis unit 200, the optical diagnosis unit 300 examines the diagnosis subject B. Here, the diagnosis subject B is in the state of being fixed by the compression pads 450.

First, the vertical transfer unit 440 may allow the X-ray detection unit 220 to descend in a direction that is away from the diagnosis subject B. When away from the diagnosis subject B by a predetermined distance, the horizontal transfer unit 430 horizontally transfers the optical detection unit 320 to locate the optical detection unit 320 below the diagnosis subject B. Then, the vertical transfer unit 440 allows the optical detection unit 320 to ascend and approach the diagnosis subject B.

Also, the optical irradiation unit 310 disposed on the second mount 520 moves to the first mount 510.

Here, the cable C for the power supply or the data communication is provided in the optical irradiation unit 310, and also, the cable is in a state of being mounted on the ring of the cable guide 530. When the cable guide 530 moves together with the optical irradiation unit 310, each of the first, second, and third links 531, 532, and 533 rotates along the movement direction of the cable C to prevent the cable C from being bent or drooping.

When the optical irradiation unit 310 moves to the first mount 510, the optical diagnosis unit 300 examines the diagnosis subject B.

In details, the optical irradiation unit 310 irradiates light to the diagnosis subject B. Here, the light irradiated from the optical irradiation unit 310 to the diagnosis subject B may be infrared light.

Thus, the light passing through the diagnosis subject B may be provided to the optical detection unit 320, and the optical detection unit 320 may acquire an optical transmission image of the diagnosis subject B through the light received thereto.

The optical diagnosis unit 300 may examine the diagnosis subject B in the state in which the optical diagnosis unit 300 rotates at the predetermined angle according to situations.

In detail, each of the optical irradiation unit 310 and the optical detection unit 320 rotates at a predetermined angle while maintaining the state in which the optical irradiation unit 310 and the optical detection unit 320 are disposed in the straight line with the diagnosis subject B. Here, since the compression pads 450 are in the state of being disposed on the transfer unit 400, the optical irradiation unit 310 and the X-ray detection unit 220 rotate together.

In this state, the diagnosis subject B may be disposed to be pressed and fixed between the compression pads 450, and the optical irradiation unit 310 and the optical detection unit 320 may irradiate the light to the diagnosis subject B to obtain the optical transmission image.

As described above, the breast cancer diagnosis device 1 according to an embodiment of the present invention may perform the examination using the X-rays and the examination using the light at once in the state in which the diagnosis subject B is pressed and fixed to significantly reduce a examination time, and thus, the number of diagnosis subjects B that is capable of being examined in a day may significantly increase to increase in profit of the hospital.

When the conventional examination using the X-rays is completed, the diagnosis subject B moves to perform the examination using the light. Here, the diagnosis subject B is examined in the state of being compressed and fixed in different states by the compression pads 450, the X-ray transmission image and the optical transmission image, which are obtained through the examination of the diagnosis subject B, may have shape, positions, states, and angles, which are different from each other. Thus, it is difficult to generate diagnosis data for determining whether lesions exist in the diagnosis subject B. That is, a series of processes in which a three-dimensional image is generated through the image information for determining whether the lesions exist in the diagnosis subject B, and diagnosis data is generated by comparing and matching the X-ray transmission image with the optical transmission image may be very complicated.

However, since the breast cancer diagnosis device 1 according to an embodiment of the present invention obtains the X-ray transmission image and the optical transmission image having the same shape, position, state, and angle through the X-ray diagnosis unit 200 and the optical diagnosis unit 300 in the state in which the diagnosis subject B is compressed and fixed, it may be easily acquired through the diagnosis data for determining whether the lesions exist in the diagnosis subject B. That is, since the diagnosis data with respect to the diagnosis subject B is generated without performing the process of matching the X-ray transmission image with the optical transmission image, the diagnosis data of the diagnosis subject B may be quickly and accurately generated.

The breast cancer diagnosis device examines the diagnosis subject through the X-ray diagnosis unit and the optical diagnosis unit in the state in which the diagnosis subject is disposed between the compression pads by the person to be diagnosed. Here, the examination of the diagnosis subject may be performed in the state in which the person to be diagnosed grasps the handle disposed on the main body to prevent the diagnosis subject fixed by the compression pads from moving. Here, since the horizontal transfer unit or the vertical transfer unit is disposed below the diagnosis subject and thus does not operate, the horizontal transfer unit or the vertical transfer unit may not invade a region in which the body of the diagnosis subject is disposed to fundamentally prevent an expected image applied to the diagnosis subject from occurring.

Here, it is preferable that each of the compression pads 450 has a structure in which the X-rays irradiated to the X-ray diagnosis unit 200 and the light irradiated to the optical diagnosis unit 300 are effectively transmitted in the state of fixing the diagnosis subject.

Figure 12:
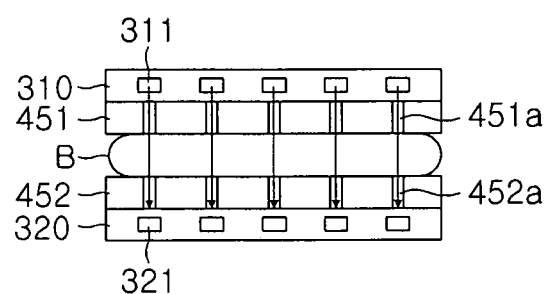
FIG. 12 is a conceptual view illustrating an optical diagnosis unit and the compression pads of the breast cancer diagnosis device according to an embodiment of the present invention.

For example, the compression pads 450 may be made of a material through which the X-rays irradiated to the X-ray diagnosis unit 200 and the light irradiated to the optical diagnosis unit 300 are transmitted without being attenuated. Furthermore, as illustrated in FIG. 12, the through-holes may pass through the compression pads 450 to significantly reduce attenuation of the light passing through the compression pads 450. In addition, since the through-holes defined in the upper plate 451 and the lower plate 452 of the compression pads 450 are defined to correspond to each other, the attenuation of the light irradiated to the optical diagnosis unit 300 may be effectively suppressed.

Figure 13:
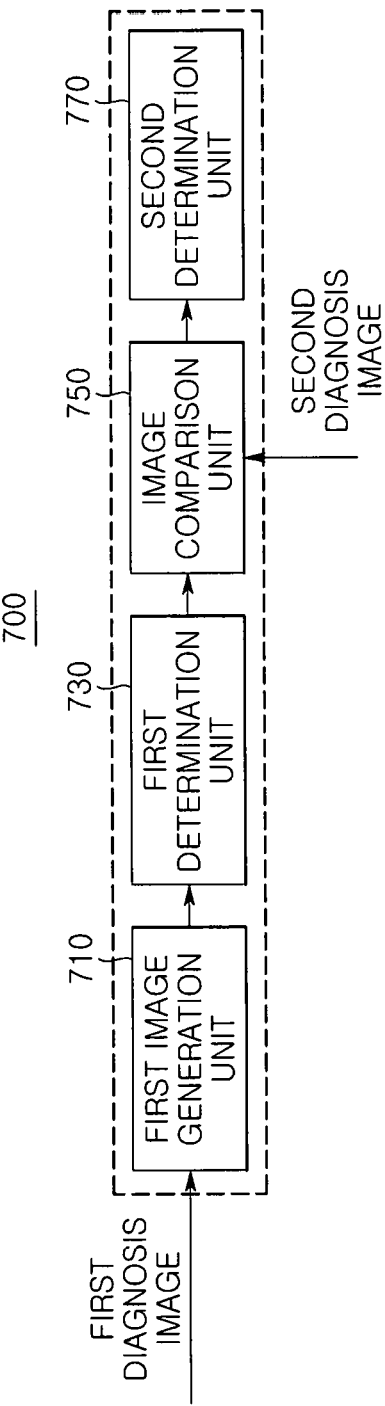
FIG. 13 is a detailed block diagram of the breast cancer diagnosis device according to an embodiment of the present invention.

Referring to FIGS. 12 and 13, the breast cancer diagnosis device 1 according to an embodiment of the present invention may further include a lesion determination unit 700 for determining whether the lesions (breast cancer lesions in the breast) exist in the diagnosis subject B by using the X-ray transmission image and the optical transmission image, which are acquired through the X-ray diagnosis unit 200 and the optical diagnosis unit 300.

Here, the lesion determination unit 700 may generate a fusion image by fusing the optical transmission image and the X-ray transmission image sequentially photographed in the state in which the diagnosis subject is constantly fixed to effectively determine whether the lesions exist in the diagnosis subject.

The lesion determination unit 700 includes a first image generation unit 710, a second image generation unit 720, a first determination unit 730, an image comparison unit 750, and a second determination unit 770.

The first image generation unit 710 generates a first three-dimensional image with respect to the diagnosis subject B by using the X-ray transmission image acquired in the X-ray detection unit 220, and the first determination unit 730 determines a lesion suspicious portion in the diagnosis subject B by using the first three-dimensional image.

Here, since the first three-dimensional image is a three-dimensional single layer image in a digital breast tomosynthesis (DBT) manner, which is generated by synthesizing the X-ray transmission image in a filtered backprojection (FBP) manner, the first determination unit 730 may detect a breast mass and microcalcification within the diagnosis subject B by using the first three-dimensional image to determine the microcalcified region as the lesion suspicious portion.

The second image generation unit 720 generates a second three-dimensional image with respect to the diagnosis subject B by using the optical transmission image acquired in the optical detection unit 320.

The optical transmission image includes information according to phenomena (for example, scattering, reflection, or absorption) occurring in each of components (for example, muscles, cancer cells, mammary glands, blood vessels, etc. in the subject B) of the diagnosis subject B through the infrared light irradiated to the diagnosis subject B by the optical irradiation unit 310.

The second three-dimensional image may generate a three-dimensional single image in a diffuse optical tomography (DOT), which has high resolution and ancient roughness by applying a repetitive algorithm based on compression sensing to the optical transmission image.

Also, the first determination unit 730 may be a computer-aided detection (CAD) module for automatically or semi-automatically detecting lesions by using the X-ray transmission image or the first three-dimensional image.

The image comparison unit 750 compares the lesion suspicious portion with the optical transmission image acquired in the optical detection unit 320. That is, the image comparison unit 750 may compare the lesion suspicious portion with the second three-dimensional image after the second three-dimensional image with respect to the diagnosis subject B is generated, in only a region corresponding to the lesion suspicious portion of the entire region constituting the optical transmission image by using the optical transmission image.

The image comparison unit 750 may compare the lesion suspicious portion with the second three-dimensional image to grasp whether the lesion suspicious portion corresponds to an actual lesion.

The second determination unit 770 may determine whether the lesions exist in the diagnosis subject B by comparing the lesion suspicious portion with the second three-dimensional image, which is performed by the image comparison unit 750.

Also, the second determination unit 770 may be a computer-aided diagnosis (CADx) module that utilizes one or a combination of the X-ray transmission image, the first three-dimensional image, the optical transmission image, and the second three-dimensional image.

As described above, a reason in which whether the lesions exist in the diagnosis subject B is determined by utilizing all of the first three-dimensional image and the second three-dimensional image is for finally determining whether the lesions exist in the diagnosis subject B by using the second three-dimensional image generated with respect to the lesion suspicious portion (i.e., by utilizing color information included in the second three-dimensional image) because of a limitation in determining whether the lesion suspicious portion corresponds to the actual lesion although the first three-dimensional image is easily utilized in determining the lesion suspicious portion. In this case, the first three-dimensional image and the second three-dimensional image may be complementarily utilized to significantly improve accuracy with respect to the determination whether the lesions exist in the diagnosis subject B.

In addition, when the second three-dimensional image is generated with respect to the entire region constituting the optical transmission image, there is a problem that it takes a lot of time (approximately 1 to 2 hours) until the generation of the second three-dimensional image is completed. As described above, when the second three-dimensional image is generated with respect to only the lesion suspicious portion, the generation completion time may be significantly reduced.

Figure 14:
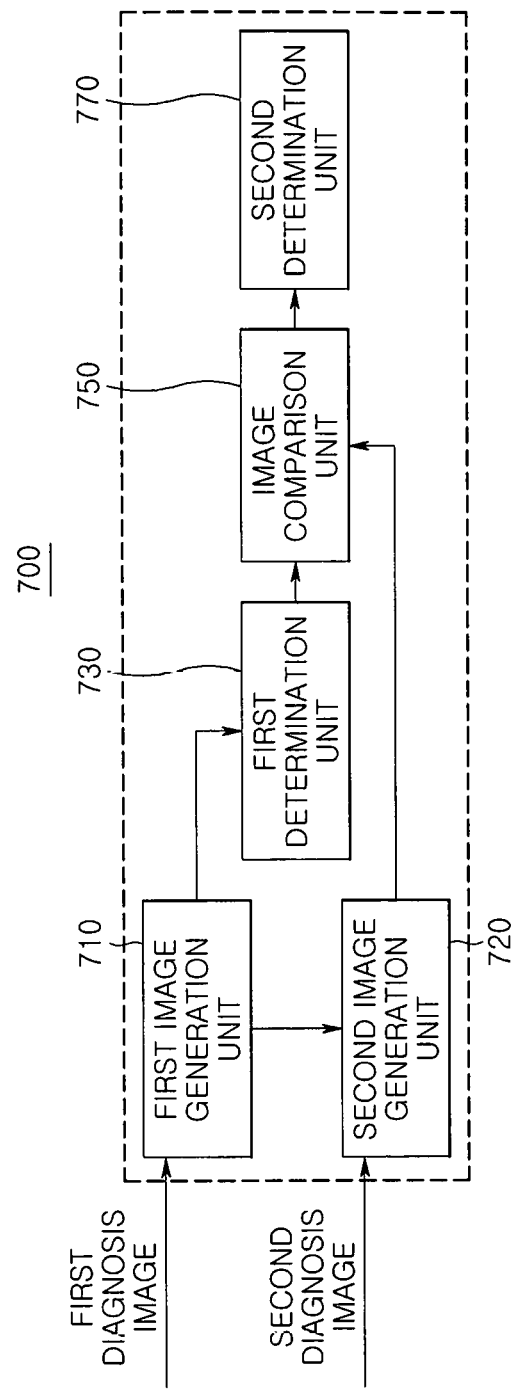
FIG. 14 is a detailed block diagram illustrating a lesion determination unit of the breast cancer diagnosis device according to an embodiment of the present invention.

Also, in the constituents of the lesion determination unit 700, as illustrated in FIG. 14, the first image generation unit 710 generating the first three-dimensional image with respect to the diagnosis subject B from the X-ray transmission image and the second image generation unit 720 generating the second three-dimensional image with respect to the diagnosis subject B from the optical transmission image may be respectively provided to compare the lesion suspicious portion with the second three-dimensional image in the image comparison unit 750 and then determine whether the lesions exist in the diagnosis subject B according to the comparison result in the second determination unit 770.

In this case, although the second image generation unit 720 generates the second three-dimensional image with respect to the entire region constituting the optical transmission image, contour information with respect to the breast mass and the microcalcification included in the first three-dimensional image may be transmitted to the second image generation unit 720 prior to the generation of the second three-dimensional image. Then, the second image generation unit 720 may reflect the contour information to the process for generating the second three-dimensional image (i.e., add the contour information to a cost function of the repetitive algorism) to significantly reduce a generation rate of the second three-dimensional image.

Figure 15:
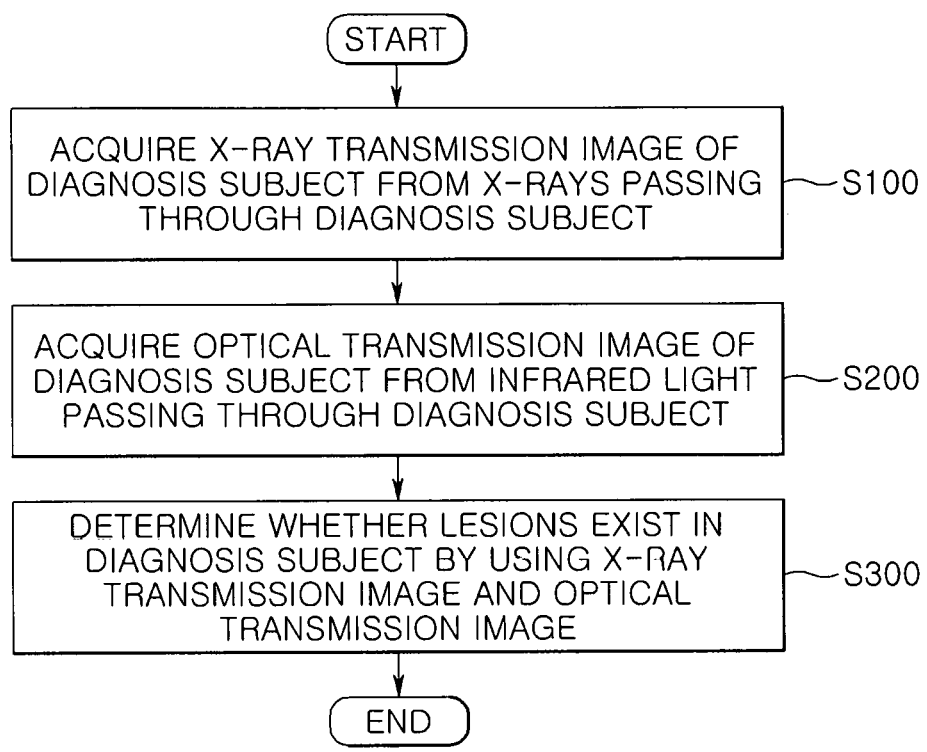
FIG. 15 is a flowchart illustrating a method of diagnosing breast cancer by using the breast cancer diagnosis device according to an embodiment of the present invention.

FIG. 15 is a flowchart illustrating a process of diagnosing the breast cancer by using the breast cancer diagnosis device 1 according to an embodiment of the present invention.

As illustrated in FIG. 15, in operation S100, an X-ray detection unit 220 acquires an X-ray transmission image with respect to a diagnosis subject B from X-rays, which passes through the diagnosis subject B after being irradiated from an X-ray irradiation unit 210.

In operation S200, an optical detection unit 320 acquires an optical transmission image with respect to the diagnosis subject B from the X-rays which passes through the diagnosis subject B after being irradiated from an optical irradiation unit 310.

In operation S300, when a lesion determination unit determines whether lesions exist in the diagnosis subject B by using the X-ray transmission image and the optical transmission image, the process is ended.

Here, detailed processes in operation S300 will be described in detail with reference to FIG. 16.

FIG. 16 is a detailed flowchart illustrating operation S300 of FIG. 15. As illustrated in FIG. 16, in operation S310, a first image generation unit 710 generates a first three-dimensional image with respect to the diagnosis subject B from the X-ray transmission image.

Here, since the process of generating the first three-dimensional image from the X-ray transmission image is explained as described above, its detailed description will be omitted.

In operation S330, a first determination unit 730 determines a lesion suspicious portion by using the first three-dimensional image, and in operation S350, an image comparison unit 750 compares the lesion suspicious portion with the optical transmission image.

Here, in operation S350, the image comparison unit 750 may compare the lesion suspicious portion with the second three-dimensional image after the second three-dimensional image with respect to the diagnosis subject B is generated, in only a region corresponding to the lesion suspicious portion of the entire region constituting the diagnosis image by using the optical transmission image.

In operation S370, when a second determination unit 770 determines whether the lesions exist in the diagnosis subject B according to the comparison result by comparing the lesion suspicious portion with the second three-dimensional image, which is performed by the image comparison unit 750, the process is ended.

The above-disclosed subject matter is to be considered illustrative, and not restrictive, and the appended claims are intended to cover all such modifications, enhancements, and other embodiments, which fall within the true spirit and scope of the present invention. Therefore, the embodiments disclosed in the present invention and the accompanying drawings are intended to illustrate and not to limit the technical spirit of the present invention, and the scope of the technical idea of the present invention is not limited by these embodiments and the accompanying drawings. Therefore, the scope of the invention is defined not by the detailed description of the invention but by the appended claims, and all differences within the scope will be construed as being included in the present invention.

The invention claimed is:

1. A breast cancer diagnosis device comprising:
   an X-ray diagnosis unit generating an X-ray transmission image of a diagnosis subject;
   an optical diagnosis unit generating an optical transmission image of the diagnosis subject;
   compression pads pressing and fixing upper and lower portions of the diagnosis subject at a predetermined pressure so that the X-ray diagnosis unit and the optical diagnosis unit sequentially generate the X-ray image and the optical transmission image while the compression pads fix the diagnosis subject;
   a transfer unit which is coupled to the X-ray diagnosis unit and the optical diagnosis unit to transfer all or part of the X-ray diagnosis unit and the optical diagnosis unit, and sequentially transfer all or part of the X-ray diagnosis unit or the optical diagnosis unit toward the diagnosis subject; and
   a lesion determination unit for fusing the optical transmission image and the X-ray transmission image, which are sequentially photographed in a state in which the diagnosis subject is constantly fixed to generate a fusion image, wherein the X-ray diagnosis unit comprises:

an X-ray irradiation unit generating X-rays to irradiate the X-rays onto the diagnosis subject; and an X-ray detection unit disposed to face the X-ray irradiation unit to acquire an X-ray diagnosis image of the diagnosis subject from the X-rays, which are irradiated from the X-ray irradiation unit to pass through the diagnosis subject, wherein the optical diagnosis unit comprises:

an optical irradiation unit irradiating light onto the diagnosis subject; and an optical detection unit disposed to face the optical irradiation unit to acquire an optical diagnosis image of the diagnosis subject from the light, which is irradiated from the optical irradiation unit to pass through the diagnosis subject, wherein the transfer unit comprises a horizontal transfer unit coupled to the X-ray detection unit and the optical detection unit to horizontally transfer the X-ray detection unit and the optical detection unit, and the transfer unit moves the X-ray detection unit and the optical detection unit to sequentially place the X-ray detection unit and the optical detection unit in a straight line with the diagnosis subject while the compression pads fix the diagnosis subject, wherein the lesion determination unit generating a first three-dimensional image in a digital breast tomosynthesis (DBT) manner by synthesizing the X-ray transmission image in a filtered back projection (FBP) manner, generating a second three-dimensional image in a diffuse optical tomography (DOT) manner based on the optical transmission image, and determining whether one or more lesions exist in the diagnosis subject using the first three-dimensional image and the second three-dimensional image.

2. The breast cancer diagnosis device of claim 1, wherein the transfer unit comprises a vertical transfer unit selectively coupled to one of the X-ray detection unit and the optical irradiation unit or the optical detection unit to vertically transfer one of the X-ray detection unit and the optical irradiation unit or the optical detection unit and thereby to approach the diagnosis subject.

3. The breast cancer diagnosis device of claim 1, wherein the transfer unit is coupled to the X-ray detection unit and the optical irradiation unit or the optical detection unit, and the X-ray detection unit and the optical irradiation unit or the optical detection unit are disposed on the same panel.

4. The breast cancer diagnosis device of claim 3, wherein the transfer unit sequentially transfers the X-ray detection unit and the optical irradiation unit or the optical detection unit to sequentially generate the X-ray diagnosis image and the optical diagnosis image of the diagnosis subject.

5. The breast cancer diagnosis device of claim 1, wherein the transfer unit comprises a rotation unit allowing at least one of the X-ray diagnosis unit and the optical diagnosis unit to rotate about the diagnosis subject.

6. The breast cancer diagnosis device of claim 5, wherein the rotation unit comprises a first rotation member disposed above the diagnosis subject to allow the X-ray irradiation unit and the optical irradiation unit or the optical detection unit to rotate about the diagnosis subject.

7. The breast cancer diagnosis device of claim 5, wherein the rotation unit comprises a second rotation member disposed below the diagnosis subject to allow the X-ray detection unit and the optical irradiation unit or the optical detection unit to rotate about the diagnosis subject.

8. The breast cancer diagnosis device of claim 1, wherein the compression pads comprise:

an upper plate disposed on the diagnosis subject to come into contact with the upper portion of the diagnosis subject; and a lower plate disposed to face the upper plate and disposed on a lower portion of the diagnosis subject to come into contact with the lower portion of the diagnosis subject.

9. The breast cancer diagnosis device of claim 8, wherein the compression pads press the diagnosis subject that is disposed between the upper plate and the lower plate through ascending and descending of at least one of the upper plate and the lower plate.

10. The breast cancer diagnosis device of claim 8, wherein each of the compression pads is made of a material through which wavelengths of the X-rays used for the X-ray transmission image and the light used for the optical transmission image are transmitted.

11. The breast cancer diagnosis device of claim 8, wherein one or more through-holes through which the light used for generating the optical transmission image passes are provided in the upper plate and the lower plate constituting the compression pads, and the through-holes of the upper plate and the through-holes of the lower plate are defined in positions corresponding to each other.

12. The breast cancer diagnosis device of claim 1, further comprising a mount unit disposed adjacent to the transfer unit so that one of the optical irradiation unit and the optical detection unit is disposed above the diagnosis subject.

13. The breast cancer diagnosis device of claim 12, wherein the mount unit comprises:

a first mount supporting the optical irradiation unit and the optical detection unit so that the optical irradiation unit and the optical detection unit are disposed in the straight line with the diagnosis subject; and a second mount supporting the optical irradiation unit and the optical detection unit so that the optical irradiation unit and the optical detection unit are disposed outside a region in which the X-ray diagnosis unit diagnoses the diagnosis subject.

14. The breast cancer diagnosis device of claim 13, wherein a cable for supplying power and transmitting or receiving data is provided in the optical irradiation unit or the optical detection unit, and a cable guide supporting the cable provided in the optical irradiation unit or the optical detection unit while moving the cable to prevent the cable from being bent or drooping to the bottom is provided.

15. The breast cancer diagnosis device of claim 14, wherein the cable guide comprises:

a first link disposed adjacent to the transfer unit;

a second link rotatably coupled to the first link; and a third link rotatably coupled to the second link and comprising a ring on which the cable is mounted.

16. The breast cancer diagnosis device of claim 1, wherein the lesion determination unit comprises:

a first image generation unit generating the first three-dimensional image with respect to the diagnosis subject by using the X-ray transmission image acquired in the X-ray detection unit;

a first determination unit determining a lesion suspicious portion in the diagnosis subject by using the first three-dimensional image;

a second image generation unit generating the second three-dimensional image with respect to the diagnosis subject by using the optical transmission image acquired in the optical detection unit;

an image comparison unit comparing the lesion suspicious portion with the optical transmission image acquired in the optical detection unit; and a second determination unit determining whether the lesions exist in the diagnosis subject by comparing the lesion suspicious portion with the second three-dimensional image, which is performed by the image comparison unit.

\* \* \* \* \*